(12) United States Patent
Huang et al.

(10) Patent No.: US 11,255,938 B2
(45) Date of Patent: Feb. 22, 2022

(54) MUTLI-SHOT MAGNETIC RESONANCE IMAGING SYSTEM AND METHOD

(71) Applicant: KONINKLIJKE PHILIPS N.V., Eindhoven (NL)

(72) Inventors: Feng Huang, Eindhoven (NL); Zhigang Wu, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 694 days.

(21) Appl. No.: 15/517,998

(22) PCT Filed: Oct. 13, 2015

(86) PCT No.: PCT/EP2015/073728
§ 371 (c)(1),
(2) Date: Apr. 10, 2017

(87) PCT Pub. No.: WO2016/059085
PCT Pub. Date: Apr. 21, 2016

(65) Prior Publication Data
US 2017/0307707 A1 Oct. 26, 2017

(30) Foreign Application Priority Data

Oct. 13, 2014 (WO) ................ PCT/CN2014/088457
Dec. 11, 2014 (EP) .................................. 14197391.7

(51) Int. Cl.
*G01R 33/483* (2006.01)
*G01R 33/561* (2006.01)
(Continued)

(52) U.S. Cl.
CPC ........ *G01R 33/4835* (2013.01); *A61B 5/7207* (2013.01); *G01R 33/4824* (2013.01);
(Continued)

(58) Field of Classification Search
CPC .......... G01R 33/56509; G01R 33/5611; G01R 33/561; G01R 33/543; G01R 33/567
See application file for complete search history.

(56) References Cited

U.S. PATENT DOCUMENTS 4,804,949 A * 2/1989 Faulkerson ......... G06F 3/03543
235/462.45
5,987,167 A * 11/1999 Inoue .................... G06T 11/001
358/518
(Continued)

FOREIGN PATENT DOCUMENTS

WO 20140037868 A1 3/2014

OTHER PUBLICATIONS

Shi X. et al.: "Motion Artifact Correction in 3D Multishot EPI-DTI with Real-Time 2D Navigators",Proceedings of the International Societyfor Magnetic Resonance in Medicine, 14th Meeting Proceedings, May 6, 2006 (May 6, 2006), p. 2982.
(Continued)

*Primary Examiner* — Ming Wu (57) ABSTRACT

The present invention provides a magnetic resonance imaging system for imaging a subject by a multi-shot imaging. The magnetic resonance imaging system comprises an acquiring unit for acquiring MR raw data corresponding to a plurality of shots; an imaging unit for generating a plurality of folded images from the MR raw data, wherein each of the plurality of folded images is generated from a subset of the MR raw data; a deriving unit for deriving magnitude of each pixel of each folded image; a detecting unit for detecting a motion of the subject during the multi-shot imaging based on similarity measurements of any two folded images of the plurality of folded images, wherein the detecting unit further comprises a first deriving unit configured to derive the measured similarities; and a reconstructing unit for reconstructing a MR image of the subject based on MR raw data
(Continued)

obtained according to a detection result of the detecting unit. Since the partially acquired MR raw data is used for motion detection directly, it would be more rapid and stable.

14 Claims, 4 Drawing Sheets

(51) Int. Cl.
  *G01R 33/565* (2006.01)
  *A61B 5/00* (2006.01)
  *G01R 33/48* (2006.01)
  *G01R 33/563* (2006.01)
  *A61B 5/055* (2006.01)

(52) U.S. Cl.
  CPC ...... *G01R 33/4833* (2013.01); *G01R 33/5611* (2013.01); *G01R 33/5615* (2013.01); *G01R 33/56308* (2013.01); *G01R 33/56509* (2013.01); *A61B 5/055* (2013.01); *G01R 33/5616* (2013.01); *G01R 33/5617* (2013.01); *G01R 33/56341* (2013.01)

(56) References Cited

U.S. PATENT DOCUMENTS

| | | | |
|---|---|---|---|
| 8,155,389 | B2 | 4/2012 | Parker et al. |
| 8,427,153 | B2 | 4/2013 | Hu et al. |
| 2004/0102695 | A1* | 5/2004 | Stergiopoulos .... G01R 33/5673 600/413 |
| 2005/0240099 | A1* | 10/2005 | Sun .................... A61B 5/055 600/410 |
| 2009/0085563 | A1 | 4/2009 | Bito et al. |
| 2009/0087057 | A1 | 4/2009 | Parker et al. |
| 2011/0105882 | A1 | 5/2011 | Lake et al. |
| 2012/0002859 | A1 | 1/2012 | Huang et al. |
| 2012/0099774 | A1* | 4/2012 | Akcakaya ............... G06T 5/002 382/131 |
| 2012/0235679 | A1 | 9/2012 | Xue et al. |
| 2014/0002078 | A1 | 1/2014 | Chen et al. |
| 2015/0212182 | A1 | 7/2015 | Nielsen et al. |

OTHER PUBLICATIONS

Nielsen T, Börnert P. "Iterative Motion Compensated Reconstruction for Parallel Imaging Using an Orbital Navigator" Magn Reson Med 2011;6(5); 1339-1345.

Jeong H-K, Gore JC, Anderson AW. "High-Resolution Human Diffusion Tensor Imaging Using 2-D Navigated Multishot Sense EPI at 7 T" Magn Reson Med 2013;69:793-802.

Liu C, Bammer R, Kim D, Moseley M. "Self-navigated interleaved spiral (SNAILS): application to high-resolution diffusion tensor imaging" Magn Reson Med 2004;52:1388-1396.

Chen N-k, Guidon A, Chang H-C, Song AW. A robust multi-shot scan strategy for high-resolution diffusion weighted MRI enabled by multiplexed sensitivity-encoding (MUSE). NeuroImage 2013;72:41-47.

\* cited by examiner

MUTLI-SHOT MAGNETIC RESONANCE IMAGING SYSTEM AND METHOD

CROSS REFERENCE TO RELATED APPLICATIONS

This application is a U.S. national phase application of International Application No. PCT/EP2015/073728, filed on Oct. 13, 2015, which claims the benefit of EP Application Serial No. 14197391.7 filed on Dec. 11, 2014 and PCT/CN2014/088457 filed Oct. 13, 2014, each of which are incorporated herein by reference.

FIELD OF THE INVENTION

The present invention generally relates to system and method for imaging a subject, e.g., a patient, by a multi-shot imaging, especially to motion detection and/or correction during the multi-shot imaging.

BACKGROUND OF THE INVENTION

Multi-shot imaging are widely adopted in clinical magnetic resonance imaging (MRI) applications to obtain high spatial resolution diagnostic information. Two common multi-shot MR imaging methods are known as: multi-shot Turbo-spin echo (TSE) and multi-shot echo-planar imaging (ms-EPI). These imaging methods can be used to obtain high-spatial-resolution diffusion-weighted imaging (DWI). However, inter-shot motion is almost inevitable and can lead to reduced image quality in multi-shot MR images due to motion artifacts. Further, as multi-shot methods require multiple acquisitions, they may require longer acquisition times than are required for single-shot acquisitions. These longer acquisition times may exacerbate inter-shot motion.

Conventional navigator based methods use low resolution image and high resolution image with fully acquired data to detect inter-shot motion during multi-shot imaging. However, it is time consuming and may introduce mis-registration issue between the navigator and the imaging data, which degrades image quality also. In addition, non-Cartesian trajectory can be used for self-navigated multi-shot imaging method; and parallel imaging method can be used to reconstruct an un-aliased image with partially acquired data for inter-scan motion correction. However, non-Cartesian based self-navigated method needs Non-Cartesian imaging, which is still not stable clinically, and the parallel imaging method needs parallel imaging based reconstruction, which needs additional computational cost.

US2012235679A1 discloses a motion compensation method where inverse-consistent non-rigid registration is used to determine motion between shots. US2009087057A1 addresses the problem of motion correction by evaluating k-space data. WO2014037868A1 discloses a magnetic resonance imaging system with navigator-based motion detection.

SUMMARY OF THE INVENTION

Therefore, it would be desirable to provide system and method for detecting and/or correcting inter shot-motion during multi-shot imaging of a subject, e.g., a patient, which is stable and time saving and may improve image quality of the MR image by reducing the motion artifacts existing in the MR raw data.

The present invention provides a magnetic resonance imaging system for imaging a subject by a multi-shot imaging. The magnetic resonance imaging system comprises an acquiring unit for acquiring MR raw data corresponding to a plurality of shots; an imaging unit for generating a plurality of folded images from the MR raw data, wherein each of the plurality of folded images is generated from a subset of the MR raw data; a deriving unit for deriving magnitude of each pixel of each folded image; a detecting unit for detecting a motion of the subject during the multi-shot imaging based on similarity measurements of any two folded images of the plurality of folded images, wherein the detecting unit 14 further comprises a first deriving unit 201 configured to derive the measured similarities; and a reconstructing unit for reconstructing a MR image of the subject based on MR raw data obtained according to a detection result of the detecting unit 14.

Actually, the gist of the invention is that if the subject does not move during the multi-shot imaging, the magnitudes of corresponding pixels of any two of the folded images will not change, i.e., there is no discrepancy among the two folded images, as long as the folded images are generated from a same amount of MR raw data acquired corresponding to at least one successive shot.

According to the invention, part of the MR raw data, i.e., partially acquired data in a K space, during a multi-shot imaging is directly used to generate folded images and the inter-shot motion is detected based on the magnitude of each pixel of the folded images. Since there is no need to generate fully acquired data, it would save time and thus be more cost effective.

In one embodiment, the acquiring unit acquires a same amount of MR raw data for each shot of the plurality of shots; the imaging unit generates each of the plurality of folded images from the subset of the MR raw data including the same amount of MR raw data acquired for one shot; and wherein the any two different folded images are generated from MR raw data acquired for two successive shots respectively.

According to this embodiment, each of the folded images is generated from the same amount of MR raw data acquired for one shot and the shots for generating any two successive folded images are successive also. In this way, it would be possible to detect inter-shot motion based on the magnitudes of corresponding pixels of any two successive folded images corresponding to any two successive shots respectively; therefore, the inter-shot motion among any two successive shots may be detected and thus more accurate motion detection during the multi-shot imaging may be achieved.

In another embodiment, the detecting unit comprises a comparing unit for comparing the magnitudes of corresponding pixels of the any two different folded images with each other to obtain a comparing result; and a first determining unit for determining whether the motion of the subject occurs during the multi-shot imaging of the subject based on the comparing result to obtain a determining result. By means of such detecting unit, it would be possible to detect whether or not an inter-shot motion occurs among any two shots during the multi-shot imaging and thereby it provides a chance to obtain and exclude the MR raw data concerning the inter-shot motion.

In a further embodiment, the first determining unit further derives a subset of the folded images having a largest number of the folded images based on the determining results of any two folded images of the plurality of folded images, if it is determined that there is no motion to occur among any two folded images in the subset, thereby obtaining a largest static cluster of the MR raw data for generating the folded images of the subset, and the reconstructing unit reconstructs the MR image of the subject based on the largest static cluster of the MR raw data.

According to this embodiment, a final image of the subject without artifacts due to inter-shot motion may be reconstructed from the MR raw data acquired corresponding to shots among which the subject does not move, which excludes the MR raw data concerning the inter-shot motion and thus achieves the inter-shot motion correction for the final image of the subject.

In a further embodiment, the detecting unit further comprises a first deriving unit for deriving a similarity of any two folded images of the plurality of the folded images based on the magnitudes of pixels of the two folded images, the similarity being indicative of a similarity of the two folded images. The similarities are results of measurements of dissimilarity or similarity.

In one aspect, the detecting unit may further comprise a second determining unit for clustering the folded images into at least one static cluster based on the measured similarities, any two folded images of each static cluster having the similarity which indicates that the two folded images are substantially the same, the static cluster having the largest number of the MR raw data being referred to as reference cluster and the other static cluster being referred to as non-reference cluster, and wherein the reconstructing unit is configured to reconstruct the MR image of the subject based on the MR raw data of the reference cluster.

It would be preferred that the detecting unit also comprises a second deriving unit for deriving a matrix of the similarities based on the similarity measurements of any two folded images of the plurality of folded images, each element of the matrix indicative of the measured similarity of corresponding two folded images, wherein the second determining unit derives the reference cluster of the folded images based on the matrix of the similarities.

In this way, the MR image is reconstructed based on the MR raw data without relating to inter-shot motion only, thereby reducing artifacts caused by inter-shot motion in the MR image and obtaining improved image quality. In addition, by means of clustering method based on the matrix of the similarities of the folded images, it may be more feasible to obtain the MR raw data without relating to inter-shot motion.

In one aspect, the detecting unit further comprises a third determining unit configured to determine a motion parameter for a rigid motion of a folded image in the non-reference cluster relative to a folded image in the reference cluster by maximizing the similarity between the two folded images, wherein the reconstructing unit is further configured to reconstruct the MR image from the MR raw data corresponding to the plurality of shots based on the motion parameter.

In this way, a motion parameter may be calculated and thereby used for motion correction during the reconstructing of the MR raw data to obtain improved image quality. Various aspects and features of the disclosure are described in further detail below. And other objects and advantages of the present invention will become more apparent and will be easily understood with reference to the description made in combination with the accompanying drawings.

BRIEF DESCRIPTION OF THE DRAWINGS

The present invention will be described and explained hereinafter in more detail in combination with embodiments and with reference to the drawings, wherein.

The same reference signs in the figures indicate similar or corresponding feature and/or functionality.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

DETAILED DESCRIPTION OF THE EMBODIMENTS

Figure 1:
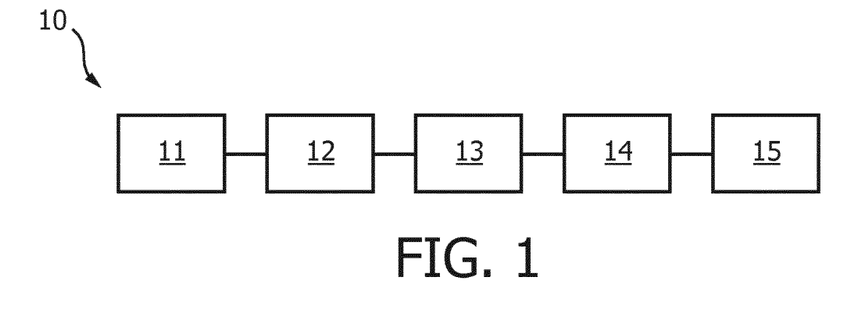
FIG. 1 is a general schematic block diagram of a magnetic resonance imaging system 10 for imaging a subject by a multi-shot imaging according to an embodiment of the present invention.

FIG. 1 shows a general schematic block diagram of a magnetic resonance imaging system 10 for imaging a subject by a multi-shot imaging according to an embodiment of the present invention. The magnetic resonance imaging system 10 includes an acquiring unit 11, an imaging unit 12, a deriving unit 13, a detecting unit 14 and a reconstructing unit 15.

The acquiring unit 11 acquires MR raw data corresponding to a plurality of shots during a multi-shot imaging of a subject, e.g., a patient. During the multi-shot imaging of the subject, only a part of MR raw data is acquired for each shot and then all the MR raw data for all shots may be used to fill a k space to produce a final image.

The imaging unit 12 generates a plurality of folded images from the MR raw data, and each of the folded images is generated from partially acquired MR raw data. The partially acquired MR raw data may be considered as a subset of the MR raw data which includes a same amount of MR raw data acquired corresponding to at least one successive shot and has at least a part of different MR raw data from other subsets.

In a first example, if the acquiring unit 11 acquires MR raw data corresponding to four shots during the multi-shot imaging of the subject and the amount of MR raw data acquired for each shot is the same, the imaging unit 12 may generates two folded images respectively for the first two successive shots and the last two successive shots.

Certainly, other number of folded images may be contemplated also as long as the amount of MR raw data used to generate each of the folded images has a same size to each other and the MR raw data used to generate each of the folded images is temporally successive, i.e., corresponding to successive shots. In a second example, it is also possible that the imaging unit 12 generates three folded images from the MR raw data corresponding to the four shots. In this case, a first folded image is generated from the MR raw data corresponding to first and second shots, a second folded image is generated from the MR raw data corresponding to second and third shots, and a third folded image is generated from the MR raw data corresponding to third and fourth shots.

It would be preferred that in a third example the MR raw data corresponding to each shot is considered to be a subset of the MR raw data and the imaging unit 12 generates each of the plurality of folded images from the subset of the MR raw data including the same amount of MR raw data corresponding to one shot. In this case, four folded images may be generated for the four shots respectively.

Furthermore, it may be possible that a different amount of MR raw data is obtained from different shots. The invention may be applied to this case as long as each of the folded images is generated from the same amount of MR raw data corresponding to at least one successive shot. For example, there are five shots of MR raw data to be acquired, 40% MR raw data for a k space is acquired for first two shots respectively and 20% MR raw data for a k space is acquired for last three shots respectively. In this case, each of the first and two shots generates a corresponding folded image, and a combination of the third and fourth shots generates a third folded image. The inter-shot motion of the subject may be detected based on the three folded images since the three folded images are generated from the same 40% of MR raw data corresponding to at least one successive shot. As understood by the skilled in the arts, in the example used herein, MR raw data acquired from different shots is spacially overlapped in k space such that a sum of MR raw data percentage for each shot exceeds 1.

Those skilled in the art may understand that the folded images may be generated from the MR raw data by Fast Fourier Transform (FFT). In particular, each subset of the MR raw data is subjected to FFT to obtain a folded image. After the FFT, the folded images are complex valued images, just like all MR images.

The deriving unit 13 derives magnitude of each pixel of each folded image from the complex value for each pixel so as to facilitate to a later determination on whether or not any two of the folded images are the same and thereby a determination on whether or not an inter-shot motion occurs among the folded images.

The detecting unit 14 detects a motion of the subject during the multi-shot imaging based on the magnitude of each pixel of any two different folded images of the plurality of folded images. It may be preferred that the any two different folded images are temporally successively acquired, i.e., corresponding to successive shots. This may be applied to real time motion detection or motion correction. For example, in the second example as mentioned above, the detecting unit 14 detects a motion of the subject during the multi-shot imaging based on the magnitude of each pixel of the first and second folded images or the second and third folded images; meanwhile, in the third example as mentioned above, the detecting unit 14 detects a motion of the subject during the multi-shot imaging based on the magnitude of each pixel of any two folded images generated from any two successive shots respectively.

However, it may be possible that the any two different folded images are immediately adjacent and acquired at intervals, or even the any two different folded image are not immediately adjacent at all.

Figure 2:
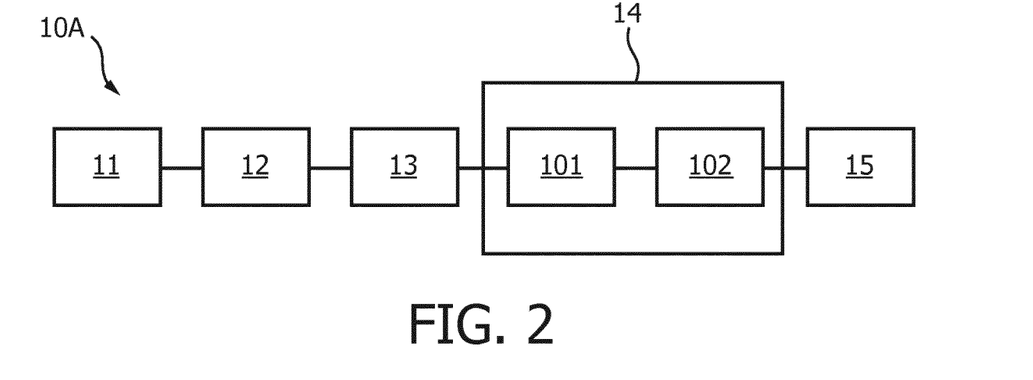
FIG. 2 is a schematic block diagram of a magnetic resonance imaging system 10A for imaging a subject by a multi-shot imaging in which a particular configuration of a detecting unit 14 is shown according to one embodiment of the present application.

FIG. 2 shows a magnetic resonance imaging system 10A for imaging a subject by a multi-shot imaging in which a particular configuration of a detecting unit 14 is shown according to one embodiment of the present application.

According to this embodiment, the detecting unit 14 includes a comparing unit 101 and a first determining unit 102. The comparing unit 101 compares the magnitudes of corresponding pixels of the any two different folded images with each other to obtain a comparing result indicative of whether or not the magnitudes of the corresponding pixels of the two folded images are all the same. The first determining unit 102 determines whether a motion occurs among the two folded images based on the comparing result. Generally, if the magnitudes of the two folded images for corresponding pixels are not the same, it may be determined that there is a motion to occur among the two folded images.

If it is determined that there is no motion to occur among any two of the folded images, the reconstructing unit 15 may use all of the MR raw data corresponding to all shots to reconstruct a final image.

However, if it is determined that there is a motion to occur among the folded images, in general, based on the determining results of any two folded images, the first determining unit 102 may be possible to find a subset of the folded images having a largest number of the folded images whose any two folded images are the same, i.e., it is determined that there is no motion to occur among any two folded images in the subset, and thereby obtain a largest static cluster of the MR raw data corresponding to the subset of the folded images. In this embodiment, the first determining unit 102 may perform a clustering algorithm to achieve the clustering of the MR raw data. In this case, the reconstructing unit 15 may reconstructs a final MR image of the subject based on the largest static cluster of the MR raw data. Considering that this may be a complex procedure a more particular and feasible mathematic method for achieving this will be introduced according to another embodiment later.

In an alternative way, if it is determined that there is a motion to occur between only two folded images and other folded images, based on the determining results of the two folded images the magnetic resonance imaging system 10 of the invention may control the acquiring unit 11 to reacquire MR raw data for generating the two folded images. After the detecting unit 14 determines that two new folded images generated from the reacquired MR raw data do not show motion compared to other original folded images, the reconstructing unit 15 may reconstruct a final MR image from all MR raw data including the reacquired MR raw data, wherein the reacquired MR raw data may replace the MR raw data for generating the two folded images showing motion compared to other folded images.

Figure 3:
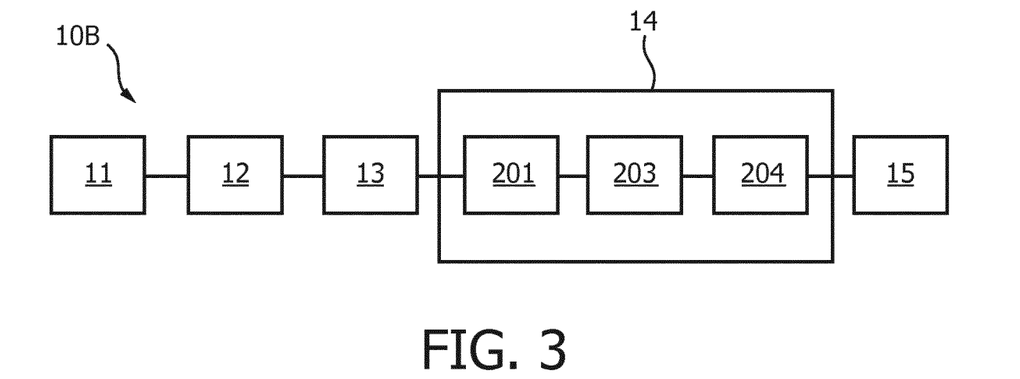
FIG. 3 is a schematic block diagram of a magnetic resonance imaging system 10B for imaging a subject by a multi-shot imaging in which a particular configuration of a detecting unit 14 is shown according to another embodiment of the present application.

FIG. 3 shows a schematic block diagram of a magnetic resonance imaging system 10B for imaging a subject by a multi-shot imaging in which a particular configuration of a detecting unit 14 is shown according to another embodiment of the present application.

The detecting unit 14 comprises a first deriving unit 201, a second deriving unit 203 and a second determining unit 204. The first deriving unit 201 derives a similarity of any two folded images of the plurality of the folded images based on the magnitudes of pixels of the two folded images, the similarity being indicative of a similarity of the two folded images. Those skilled in the art may understand that the similarity may be one of dis-similarity and similarity. In addition, those skilled in the art may understand that the similarity may be embodied as Euclidean distance or cross correlation.

Those skilled in the art may understand that each folded image may be considered to be a matrix and the magnitude for each pixel position in the folded image may be considered to be one element of the matrix, therefore, the deriving of the similarity of any two folded images may be achieved as deriving the similarity of two matrixes. Those skilled in the art would have known many methods to derive the similarity of the two matrixes.

The second deriving unit 203 receives the similarity of any two folded images from the first deriving unit 201 to form a matrix of similarities, each element of the matrix indicative of a similarity of corresponding two folded images. The second determining unit 204 clusters the folded images into at least one static cluster based on the measured similarities. Any two folded images of each static cluster have the similarity which indicates that the two folded images are substantionally the same. In other words, no inter-shot motion occurs among each static cluster. The static cluster having the largest number of the MR raw data is referred to as reference cluster, and the other static cluster is referred to as non-reference cluster. The reconstructing unit 15 further reconstructs the MR image of the subject based on the MR raw data of the reference cluster. Above clustering the folded images based on the matrix of similarities may be based on various known clustering method including but not limited to k means method.

Those skilled in the art may contemplate to omit the second deriving unit 203 and perform the clustering based on the similarities of any two folded images directly.

The second determining unit 202 determines a motion parameter of the motion of the subject among any two folded images by defining the similarity parameter of the two folded images as a function of the motion parameter and finding the motion parameter that makes the similarity parameter indicate that the two folded images are substantially the same, when the motion of the subject is a rigid motion, for example, musculoskeletal and head motion. In this case, both rotation and translation parameters may be expected to be calculated.

If the motion of the subject among the two folded images relates to translation of the subject only, the similarity parameter of the two folded images may be determined as a function of a displacement, after that, it is possible to find a displacement which makes the similarity parameter indicate that the two folded images are substantially the same by mathematic algorithms, such as method of steepest descent, which have been known for those skilled in the art. It may be contemplated that the rotation motion parameters are calculated. If the similarity parameter is a dis-similarity, a dis-similarity minimization method may be contemplated also.

If the motion parameter of the motion of the subject may be calculated, those skilled in the art would be contemplated that the reconstructing unit 15 reconstructs the MR image from the MR raw data corresponding to the plurality of shots based on the motion parameter.

Figure 4:
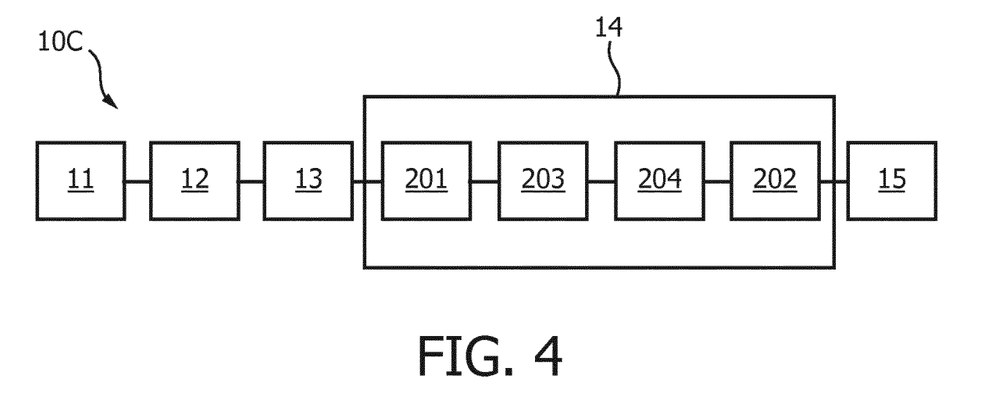
FIG. 4 shows a schematic block diagram of a magnetic resonance imaging system 10C for imaging a subject by a multi-shot imaging in which a particular configuration of a detecting unit 14 is shown according to a further embodiment of the present application.

FIG. 4 shows a schematic block diagram of a magnetic resonance imaging system 10C for imaging a subject by a multi-shot imaging in which a particular configuration of a detecting unit 14 is shown according to a further embodiment of the present application.

The detecting unit 14 further comprises a third determining unit 202. The third determining unit 202 determines a rigid motion of a folded image in the non-reference cluster relative to a folded image in the reference cluster by maximizing the similarity between the two folded images. In this case, the reconstructing unit 15 can reconstruct the MR image from the MR raw data corresponding to the plurality of shots based on the motion parameter.

Although the magnetic resonance imaging system of the invention is described by referring to the systems 10, 10A-10C shown in FIGS. 1-4, those skilled in the art would be clear that above systems may be combined or subdivided for further advantages and individual units included in above systems may be combined or subdivided also for achieving its same function.

It may be contemplated also that the individual units of the magnetic resonance imaging system of the invention may be achieved by any one of software, hardware or firmware. It may also be contemplated that the individual units of the magnetic resonance imaging system of the invention are incorporated into a processor for achieving its function.

Please note that "first", "second", "third" are used to name the units only and do not represent an order.

Figure 5:
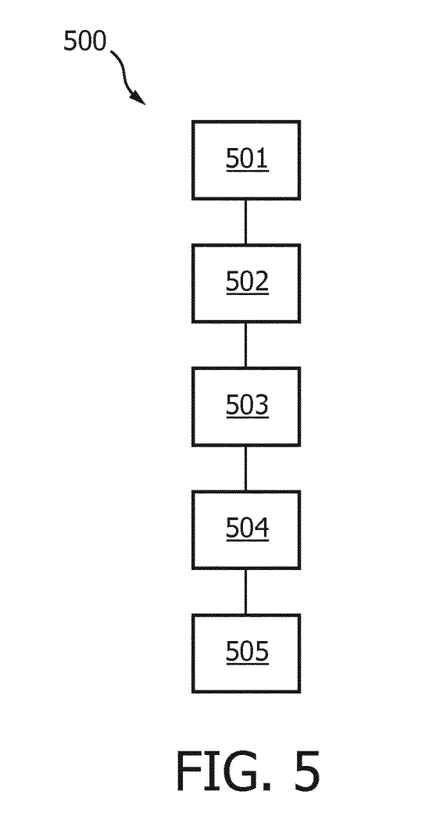
FIG. 5 is a general flow chart of a magnetic resonance imaging method 500 for imaging a subject by a multi-shot imaging according to an embodiment of the present invention.

FIG. 5 shows a general flow chart of a magnetic resonance imaging method 500 for imaging a subject by a multi-shot imaging according to an embodiment of the present invention.

In step 501, MR raw data corresponding to a plurality of shots are acquired. In step 502, a plurality of folded images are generated from the MR raw data, wherein each of the plurality of folded images is generated from a subset of the MR raw data, each subset of the MR raw data including a same amount of MR raw data acquired corresponding to at least one successive shot and having at least a part of different MR raw data from other subsets. It would be preferred that the same amount of MR raw data is acquired for only one shot of the plurality of shots and the any two different folded images are generated from MR raw data acquired for two successive shots respectively.

In step 503, magnitude of each pixel of each folded image may be derived and in step 504, a motion of the subject during the multi-shot imaging may be detected based on the magnitude of each of pixels of any two different folded images of the plurality of folded images. Step 505 is a reconstructing step for reconstructing s MR image from the MR raw data.

Figure 6:
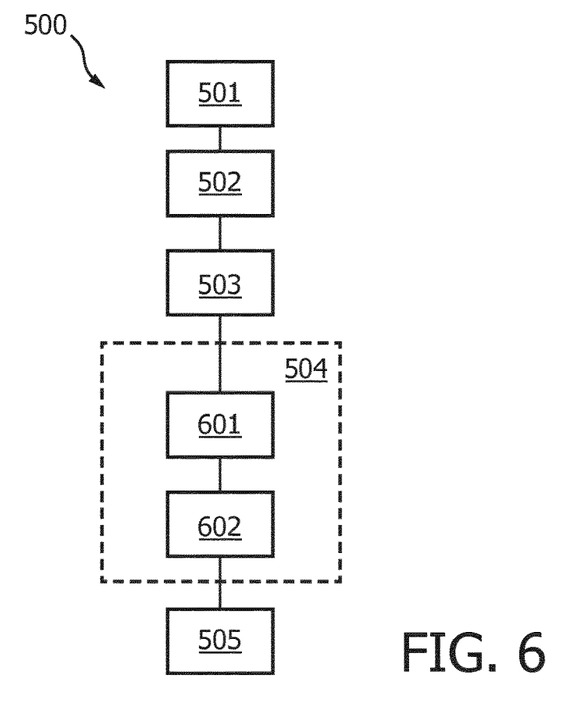
FIG. 6 is a flow chart of a magnetic resonance imaging method 500 for imaging a subject by a multi-shot imaging according to a particular embodiment of the present invention.

FIG. 6 shows a particular flow chart of a magnetic resonance imaging method 500 for imaging a subject by a multi-shot imaging according to a particular embodiment of the present invention.

According to the embodiment, the step 504 as mentioned above may be replaced by a step 601 and a step 602 to achieve an inter-shot motion detection. It may be contemplated that step 504 comprises the step 601 and 602 also.

In step 601, the magnitudes of corresponding pixels of the any two different folded images are compared with each other to obtain a comparing result. It may be contemplated that the comparing result may indicate the discrepancy between the magnitudes of corresponding pixels of the any two different folded images.

In step 602, it may be determined whether the motion of the subject occurs during the multi-shot imaging of the subject based on the comparing result, thereby obtaining a determining result. If the comparing result indicates that there is no discrepancy between the magnitudes of all corresponding pixels of the any two different folded images, it may be obvious that the two folded images are the same and thus it may be determined that there is no motion of the subject to occur among the two folded images and vice versa. In this case, a plurality of determining results may be obtained for every two folded images of the plurality of folded images to indicate whether or not the motion of the subject occurs among the two folded images.

In this embodiment, the motion of the subject may be detected.

Figure 7:
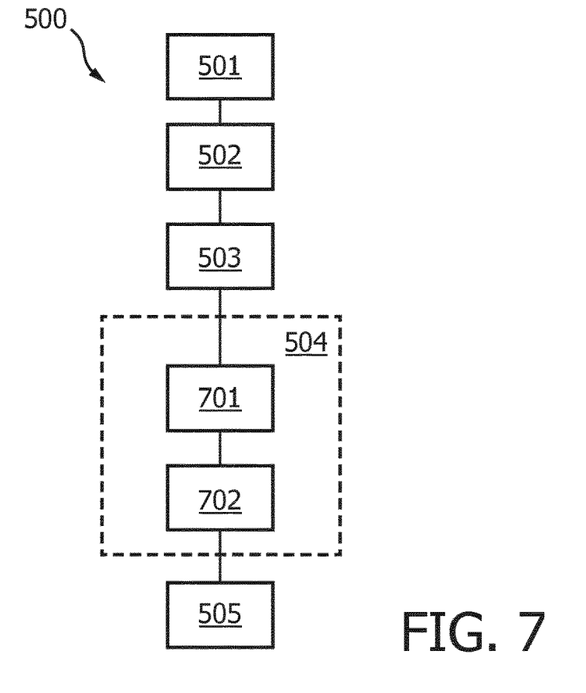
FIG. 7 is a flow chart of a magnetic resonance imaging method 500 for imaging a subject by a multi-shot imaging according to a further embodiment of the present invention.

FIG. 7 shows a particular flow chart of a magnetic resonance imaging method 500 for imaging a subject by a multi-shot imaging according to a further embodiment of the present invention.

According to the embodiment, the step 504 as mentioned above may be replaced by a step 701 and a step 702 to achieve a rigid motion parameter determination. It may be contemplated that step 504 comprises the step 701 and 702 also.

In step 701, a similarity of any two folded images of the plurality of the folded images may be derived based on the magnitudes of pixels of the two folded images, the similarity being indicative of a similarity of the two folded images.

In step 702, the folded images are clustered into at least one static cluster based on the measured similarities. Any two folded images of each static cluster have the similarity which indicates that the two folded images are substantially the same. The static cluster having the largest number of the MR raw data is referred to as reference cluster and the other static cluster is referred to as non-reference cluster.

In this embodiment, in step 505, the MR image is reconstructed from the MR raw data of the reference cluster.

Figure 8:
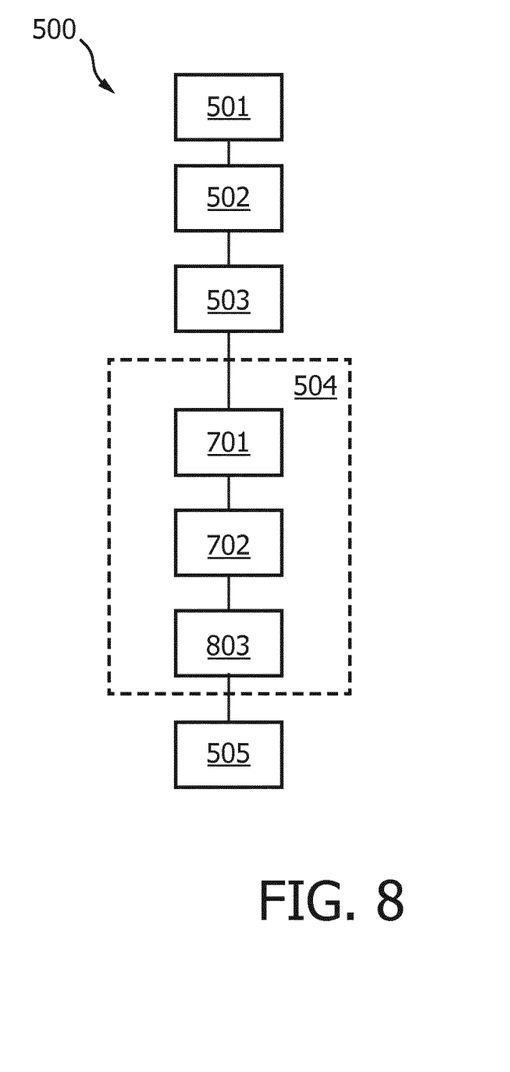
FIG. 8 is a flow chart of a magnetic resonance imaging method 500 for imaging a subject by a multi-shot imaging according to a still further embodiment of the present invention.

FIG. 8 shows a particular flow chart of a magnetic resonance imaging method 500 for imaging a subject by a multi-shot imaging according to a still further embodiment of the present invention.

According to the embodiment, a step 803 is further performed to acquire a motion parameter. In step 803, a motion parameter for a rigid motion of a folded image in the non-reference cluster relative to a folded image in the reference cluster is acquired by maximizing the similarity between the two folded images.

In this embodiment, in step 505, the MR image is reconstructed from the MR raw data corresponding to the plurality of shots based on the motion parameter.

Although the magnetic resonance imaging method has been described by referring to the magnetic resonance imaging system shown in FIGS. 1-4 respectively, it is not a limitation; those skilled in the art may combine or subdivide the steps of the method for advantages.

Please note that, the magnetic resonance imaging system according to the present invention should not be limited to that mentioned above only. It will be apparent to those skilled in the art that the various aspects of the invention claimed may be practiced in other examples that depart from these specific details.

Furthermore, the mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the product claims enumerating several units, several of these units can be embodied by one and the same item of software and/or hardware. The usage of the words first, second and third, et cetera, does not indicate any ordering. These words are to be interpreted as names.

The invention claimed is:

1. A magnetic resonance imaging system for imaging a subject by a multi-shot imaging, comprising:
    a first imaging unit configured to generate a plurality of folded images from MR raw data corresponding to a plurality of MR shots of the subject over time, wherein each folded image of the plurality of folded images is generated from a subset of the MR raw data;
    a deriving unit configured to derive magnitudes of pixels of each folded image;
    a detecting unit configured to detect an inter-shot motion of the subject during the multi-shot imaging based on similarity measurements of any two folded images of the plurality of folded images, wherein the detecting unit comprises a first determining unit configured to derive the measured similarities based on the derived magnitudes of the plurality of pixels; and
    a reconstruction unit configured to reconstruct an image of the subject excluding artifacts caused by the detected inter-shot motion.

2. The magnetic resonance imaging system of claim 1, wherein the similarity measurements measure dis-similarity or similarity.

3. The magnetic resonance imaging system of claim 1, wherein the detecting unit further comprises a second determining unit configured to cluster the folded images into at least one static cluster based on the measured similarities, any two folded images of each static cluster having the similarity which indicates that the two folded images are substantially the same, the static cluster having the largest number of the MR raw data being referred to as a reference cluster and each remaining static cluster being referred to as a non-reference cluster.

4. The magnetic resonance imaging system of claim 3, wherein the detecting unit further comprises:
    a third determining unit configured to determine a motion parameter for a rigid motion of a folded image in the non-reference cluster relative to a folded image in the reference cluster by maximizing the similarity between the two folded images.

5. The magnetic resonance imaging system of claim 3, wherein the MR image of the subject is reconstructed from the MR raw data of the reference cluster.

6. The magnetic resonance imaging system of claim 3, wherein the detecting unit further comprises:
    a second deriving unit configured to derive a matrix of the similarities based on the similarity measurements of any two folded images of the plurality of folded images, each element of the matrix indicative of the measured similarity of corresponding two folded images; wherein
the second determining unit is configured to derive the reference cluster of the folded images based on the matrix of the similarity parameters.

7. The magnetic resonance imaging system of claim 1, further comprising:
a second imaging unit configured to reconstruct a MR image of the subject based on MR raw data without the inter-shot motion obtained according to a detection result of the detecting unit.

8. A magnetic resonance imaging method for imaging a subject by multi-shot imaging, comprising:
acquiring MR raw data corresponding to a plurality of shots;
generating a plurality of folded images from the MR raw data corresponding to the plurality of shots of the subject, wherein each of the plurality of folded images is generated from a subset of the MR raw data:
deriving magnitudes of pixels of the folded images, respectively;
measuring similarities of any two folded images of the plurality of folded images using the derived magnitudes of the plurality of pixels;
detecting an inter-shot motion of the subject during the multi-shot imaging based on the measured similarities; and
reconstructing a MR image of the subject based on MR raw data without the detected inter-shot motion of the subject.

9. The magnetic resonance imaging method of claim 8, wherein detecting the inter-shot motion comprises:
clustering the folded images into at least one static cluster based on the measured similarities, any two folded images of each static cluster having the similarity which indicates that the two folded images are substantially the same;
determining the static cluster having the largest number of the MR raw data as a reference cluster; and
determining each remaining static cluster as a non-reference cluster.

10. The magnetic imaging method of claim 9, wherein detecting the inter-shot motion further comprises:
determining a motion parameter for a rigid motion of a folded image in the non-reference cluster relative to a folded image in the reference cluster by maximizing the similarity between the two folded images.

11. The magnetic imaging method of claim 9, wherein the MR image of the subject is reconstructed from the MR raw data of the reference cluster.

12. A non-transitory computer readable medium having stored thereon software instructions for imaging a subject by multi-shot imaging which, when executed by a computer, cause the computer to perform steps comprising:
generating a plurality of folded images from the MR raw data corresponding to a plurality of shots of the subject, wherein each of the plurality of folded images is generated from a subset of the MR raw data:
deriving magnitudes of pixels of the folded images, respectively;
measuring similarities of any two folded images of the plurality of folded images using the derived magnitudes of the plurality of pixels;
detecting an inter-shot motion of the subject during the multi-shot imaging based on the measured similarities; and
reconstructing a MR image of the subject based on MR raw data without the detected inter-shot motion of the subject.

13. The magnetic resonance imaging system of claim 4, wherein the MR image of the subject is reconstructed from the MR raw data corresponding to the plurality of shots based on the motion parameter.

14. The magnetic imaging method of claim 10, wherein the MR image of the subject is reconstructed from the MR raw data corresponding to the pluarity of shots based on the motion parameter.

* * * * *